(12) United States Patent
Metzger et al.

(10) Patent No.: US 6,558,355 B1
(45) Date of Patent: May 6, 2003

(54) FLUSHABLE GUIDEWIRE DEVICE

(75) Inventors: Anja Metzger, Stillwater, MN (US); Joseph J. Chang, Irving, TX (US)

(73) Assignee: Ethicon, Inc., Somerville, NJ (US)

( * ) Notice: Subject to any disclaimer, the term of this patent is extended or adjusted under 35 U.S.C. 154(b) by 50 days.

(21) Appl. No.: 09/752,793

(22) Filed: Dec. 29, 2000

(51) Int. Cl.[7] .............................. A61M 5/178

(52) U.S. Cl. ................. 604/164.13; 604/534; 600/585

(58) Field of Search ................. 604/533, 48, 164.09, 604/164.13, 164.01, 534, 535, 537; 600/433, 434, 585, 435

(56) References Cited

U.S. PATENT DOCUMENTS 5,207,648 A * 5/1993 Gross .................... 604/164.09
5,823,961 A * 10/1998 Fields et al. ................. 600/434

* cited by examiner

*Primary Examiner*—Brian L. Casler
*Assistant Examiner*—Mark Han
(74) *Attorney, Agent, or Firm*—Blakely, Sokoloff, Taylor & Zafman, LLP

(57) ABSTRACT

A guidewire handle having a first substantially cylindrical portion and a second substantially cylindrical portion. The guidewire handle has a first aperture to receive a guidewire. A second aperture is located in the first cylindrical portion and the second cylindrical portion. The second aperture is configured to allow fluid to flow therethrough.

11 Claims, 6 Drawing Sheets

```
┌─────────────────────────────────────────────────┐
│ A FLUSHABLE GUIDEWIRE ASSEMBLY IS PROVIDED IN   │
│   WHICH THE GUIDEWIRE HANDLE HAS AT             │
│   LEAST ONE APERTURE CONFIGURED TO ALLOW        │
│         FLUID TO FLOW THERETHROUGH              │
│                     200                         │
└─────────────────────────────────────────────────┘
                        │
                        ▼
┌─────────────────────────────────────────────────┐
│   COUPLING A SYRINGE TO THE GUIDEWIRE ASSEMBLY  │
│                     210                         │
└─────────────────────────────────────────────────┘
                        │
                        ▼
┌─────────────────────────────────────────────────┐
│  COMPRESSING THE SYRINGE TO CAUSE FLUID TO      │
│    FLOW THROUGH THE GUIDEWIRE ASSEMBLY          │
│                     220                         │
└─────────────────────────────────────────────────┘
```

FIG. 7

FLUSHABLE GUIDEWIRE DEVICE

BACKGROUND

1. Field of the Invention

The invention relates generally to a system to flush an intravascular assembly, and more particularly, to flush a flushable guidewire hub.

2. Background

Intravascular devices such as catheter assemblies are generally used for passing fluids between a device such as a syringe or a drip to or from body lumens such as veins or arteries, or other internal target sites. Such an assembly usually includes a hub, and a catheter tube. The tube is typically secured to the hub by means of an eyelet ring that is press fit within the nose of the hub. This hub and tube assembly is then mounted over an introducer needle comprising a sharp needle attached to a plastic hub. The sharp tip of the needle, protruding from the catheter tip, is used for piercing a body lumen so that access may be gained into the body lumen by the needle and subsequently the catheter. Once the catheter and the needle are located within the body lumen, the introducer needle is removed and discarded while the catheter tube remains in the body lumen. A syringe or a tube of a drip is then attached to the hub so that fluids may be passed through the hub and the catheter from the drip or the syringe to the body lumen. The hub is typically made of materials that provide sufficient rigidity thereto and the catheter tube is usually made of a material which is flexible.

Catheters are used in a variety of applications to communicate fluid with the body lumen of a patient. Peripherally inserted central catheters (PICCs) are one example of a catheter that are generally used for long-term vascular access. PICCs are typically inserted into a patient's arm and fed through a body lumen to a distal location, such as to a location near the central vena cava. To traverse this distance, a guidewire is often used in the catheter to route the catheter. Once located, the guidewire is removed, typically through a guidewire hub. Healthcare workers occasionally encounter resistance to catheter advancement during initial placement. In many cases, infusing a fluid through the catheter will decrease the resistance encountered and result in the successful advancement of the catheter. Conventional hubs generally have an aperture for the guidewire and for fluid to flow from a syringe through a flushable guidewire hub into a needle. The guidewire handle, however, is typically a solid piece that does not allow a syringe to be attached to the guidewire handle in order to infuse fluid therethrough. One disadvantage to this guidewire handle is that fluid does not flow as efficiently as may be necessary. It is therefore desirable to have a system that addresses this disadvantage associated with a flushable system.

SUMMARY

The invention relates to an intravascular assembly that includes a flushable guidewire device. In one embodiment, the flushable guidewire device includes a hub having a substantially first cylindrical portion and a substantially second cylindrical portion. A first aperture and a second aperture are located in the first cylindrical portion and the second cylindrical portion. The first aperture is configured to receive a guidewire. The second aperture is configured to allow fluid to flow through the first and second cylindrical portions. Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements, and in which:

FIG. 7 illustrates one method in a flow diagram for forming a one-piece guidewire hub in accordance with one embodiment of the invention.

DETAILED DESCRIPTION

The invention relates to an intravascular assembly that includes a guidewire handle that is either inserted into a conventional hub or, alternatively, forms a one-piece guidewire handle and hub. The guidewire handle includes at least two apertures. The first aperture is configured to receive a guidewire and the second aperture is configured to allow fluid to efficiently flow through the guidewire handle. In comparison, conventional guidewire handles lack an aperture or apertures to allow fluid to flow therethrough.

The following detailed description and the accompanying drawings are provided for the purpose of describing and illustrating presently preferred embodiments of the invention only, and are not intended to limit the scope of the invention in any way.

Figure 1:
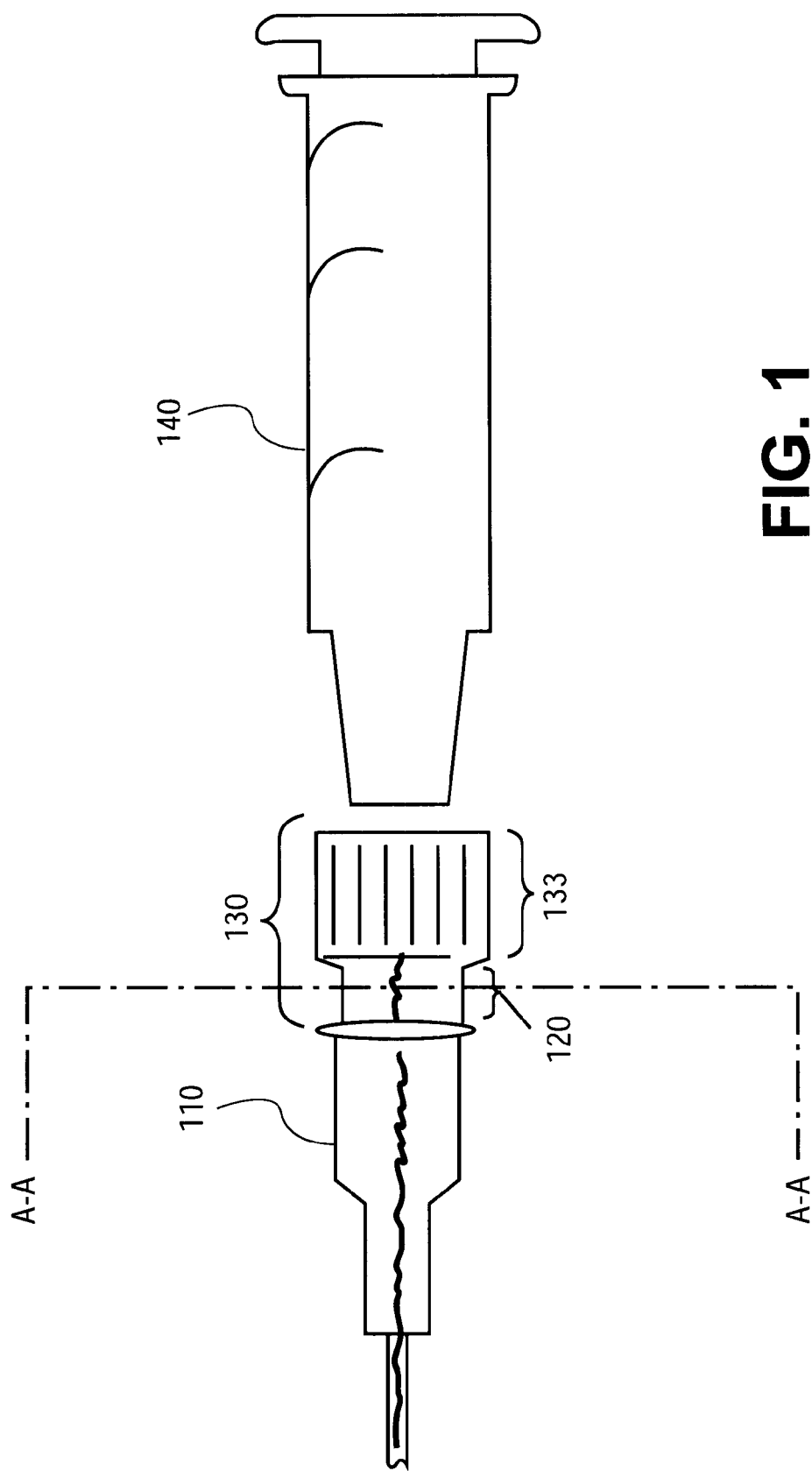
FIG. 1 illustrates a schematic cross-sectional view of flushable hub system in accordance with one embodiment of the invention.

FIG. 1 illustrates a flushable hub system in accordance with one embodiment of the invention. In this embodiment, hub 110 is coupled to guidewire handle 130 using conventional means such as using an adhesive such as Loctite 3311 commercially available from Loctite Corporation located in Rocky Hill, Conn., or other suitable adhesives.

Guidewire handle 130 includes a first substantially cylindrical portion 120 and a second substantially cylindrical portion 125. Guidewire handle 130 may be formed as a one-piece object or a two-piece object. As a two-piece object, guidewire handle 130 has first substantially cylindrical portion 120 coupled to second substantially cylindrical portion 125 using conventional means such as adhesive or thermal bonding. The purpose of the first substantially cylindrical portion 120 and the second substantially cylindrical portion 125 is to securely mate with syringe 140. Syringe 140 is inserted inside the proximal end of guidewire handle 130 and is butted against the distal end of guidewire handle 130.

Figure 2:
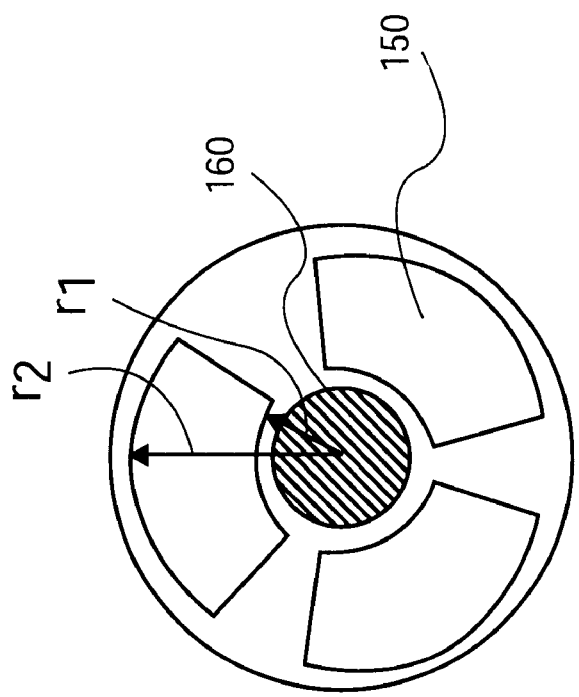
FIG. 2 illustrate a bottom view of a guidewire handle in which a plurality of apertures are located in a guidewire handle in accordance with one embodiment of the invention.

FIG. 2 illustrates a cross-sectional view of the distal end of guidewire handle 130 through line A—A of FIG. 1. FIG. 2 shows aperture 150 and aperture 160 extending through guidewire handle 130. Set of apertures 150 provides paths for fluid to pass therethrough from, for example, syringe 140. Aperture 160 is of a sufficient diameter to allow a guidewire end to be bonded inside of hub 110 using a curable adhesive, cyanoacrylate adhesives, or other suitable adhesive.

Aperture or apertures 150 are formed through drilling, or puncturing guidewire handle 130. Alternatively, injection molding may be used in which the mold for forming a one-piece guidewire handle 130 is used to form a one-piece guidewire handle (or one-piece guidewire handle and hub) ensures that the aperture is formed.

Figure 3:
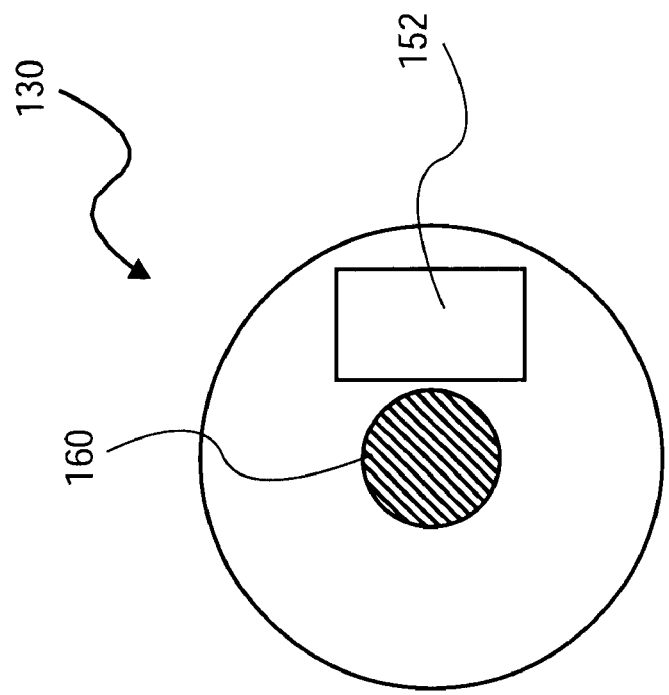
FIG. 3 illustrates a bottom view of a guidewire handle in which a substantially rectangular shaped aperture is located in a guidewire handle in accordance with one embodiment of the invention.

According to one embodiment, apertures 150 have a length of about 0.05 inches to about 0.20 inches. Additionally, apertures 150 generally have a differential radius (i.e., a second radius ($r_2$)–a first radius ($r_1$)) that ranges from about 0.02 inches to about 0.15 inches. The set of apertures 150 may take a variety of shapes. For example, FIG. 3 illustrates a cross-sectional view of the distal end of guidewire handle 130 in accordance with a second embodiment of the invention. Substantially rectangular aperture 152 is configured to allow fluid to flow therethrough. The width of aperture 152 ranges from about 0.02 inches to about 0.10 inches. The length of aperture 152 ranges from about 0.02 inches to about 0.08 inches.

Figure 5:
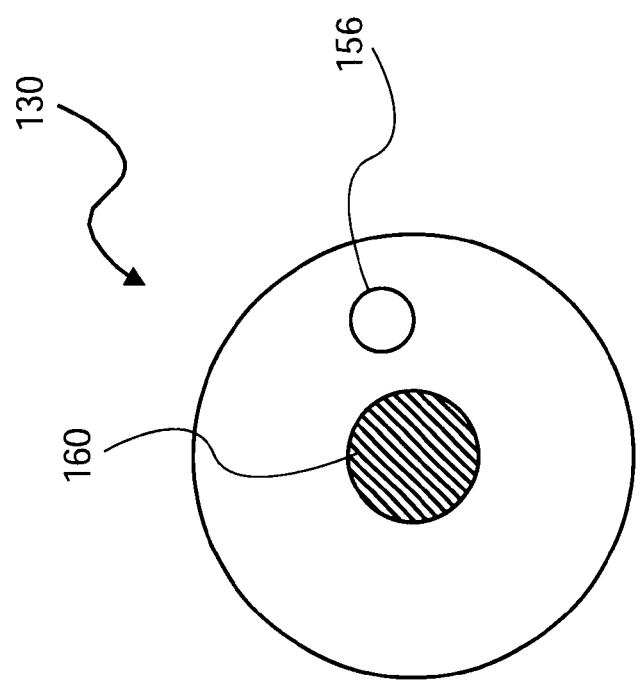
FIG. 5 illustrates a bottom view of a guidewire handle in which a substantially circular shaped aperture is located in a guidewire handle in accordance with one embodiment of the invention.
Figure 4:
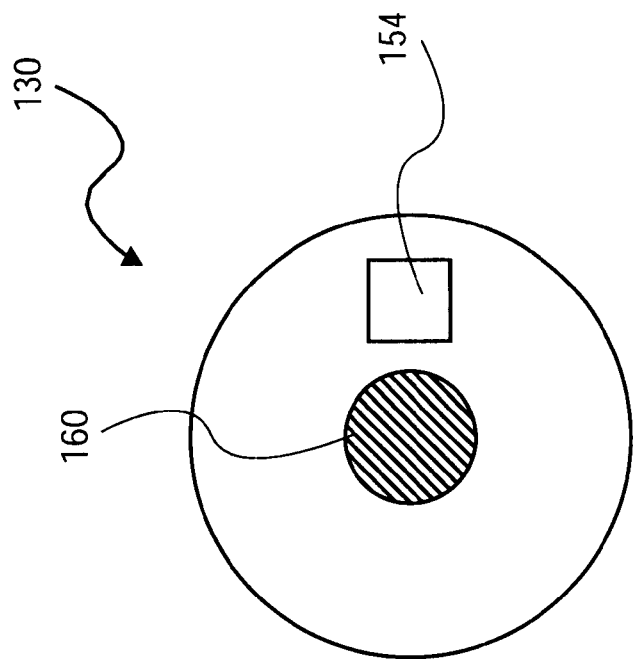
FIG. 4 illustrate a bottom view of a guidewire handle in which a substantially square shaped aperture is located in a guidewire handle in accordance with one embodiment of the invention.
Figure 6:
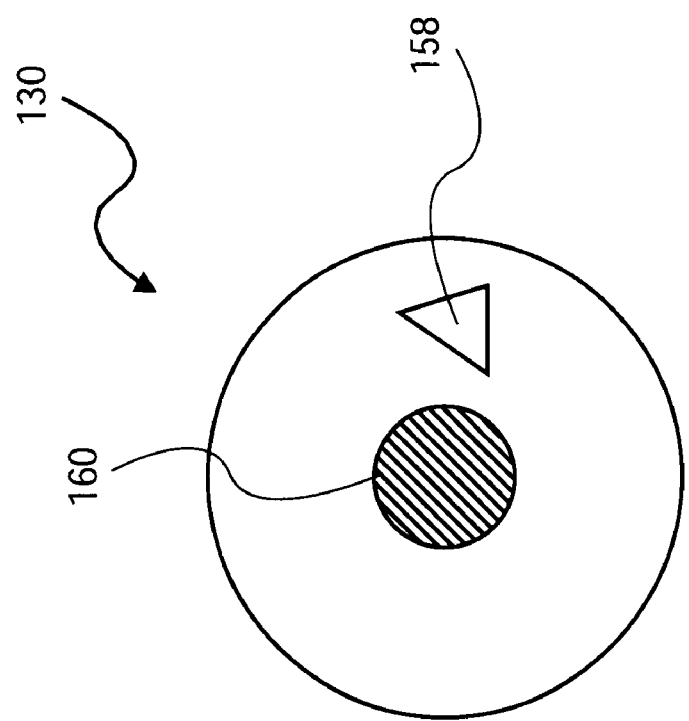
FIG. 6 illustrates a bottom view of a guidewire handle in which a substantially triangular shaped aperture is located in a guidewire handle in accordance with one embodiment of the invention.
Figure 8:
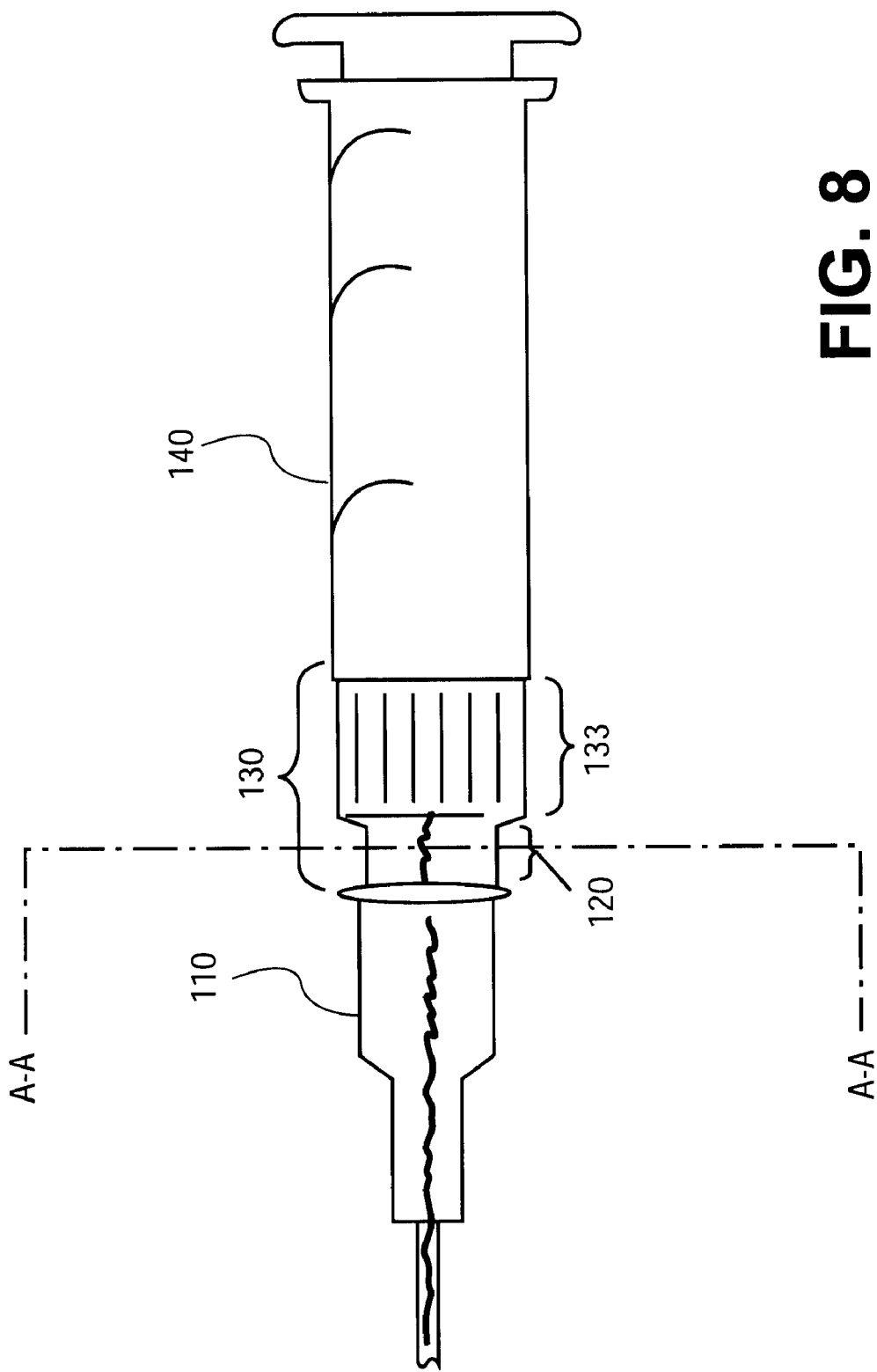
FIG. 8 illustrate a schematic cross-section view of a flushable guidewire apparatus with an inserted syringe in accordance with one embodiment of the invention.

FIG. 4 illustrates a cross-sectional view of the distal end of guidewire handle 130 in accordance with a third embodiment of the invention. Aperture 154 is substantially square in shape to allow fluid to flow therethrough. Guidewire handle 130 may have a single aperture or a plurality of apertures to allow fluid to flow through guidewire handle 130. FIG. 5 illustrates a fourth embodiment with substantially circular aperture 156 configured to allow fluid to flow through guidewire handle 130. FIG. 6 illustrates a fifth embodiment with aperture 158 of a substantially triangular in shape to allow fluid to flow through guidewire handle 130. It is appreciated that although guidewire handle 130 has been shown to include a variety of different shaped single apertures to allow fluid to flow through guidewire handle 130, guidewire handle 130 may have a plurality of apertures. Additionally, the plurality of apertures may include a variety of shapes to allow fluid to flow through guidewire handle 130. It is also appreciated that aperture 160 may be of a variety of shapes, limited only by its ability to accommodate a guidewire.

FIG. 7 illustrates a flow diagram of one method in accordance with one embodiment of the invention. At block 200, a flushable guidewire assembly is provided. The flushable guidewire assembly includes a hub coupled to a guidewire handle and to a syringe. The guidewire handle has at least one aperture or a plurality of apertures to allow fluid to flow therethrough. These apertures may have a variety of shapes such as rectangular, square, circular, triangular, or any other suitable shape. At block 210, a syringe is coupled to the guidewire assembly. The flushable guidewire assembly is inserted into a vein or an artery using a guidewire to access remote locations in the patient's body. At block 220, a fluid is flushed through the flushable guidewire assembly by compressing a syringe. This includes the fluid passing through a guidewire handle. Flushing the flushable guidewire assembly allows the guidewire to move within, for example, a vein with less resistance since the fluid, in one sense, may expand the inner diameter of the vein.

In the foregoing specification, the invention is described with reference to specific embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A guidewire handle assembly comprising:
   a first substantially cylindrical portion and a second substantially cylindrical portion;
   a first aperture located in the first substantially cylindrical portion and the second substantially cylindrical portion to receive a guidewire the guidewire attached to the second substantially cylindrical portion; and
   a second aperture configured to allow fluid to flow therethrough.

2. The guidewire handle of claim 1, wherein the second aperture has a shape that is one of substantially rectangular, square, circular, and triangular.

3. A guidewire handle comprising:
   a first substantially cylindrical portion and a second substantially cylindrical portion having a first aperture and a set of second apertures located through the first substantially cylindrical portion and the second substantially cylindrical portion, the first aperture to receive a guidewire and the set of second apertures configured to allow fluid to flow therethrough the second substantially cylindrical portion for attachment to the guidewire.

4. The guidewire handle of claim 3, wherein apertures of the set of second apertures are about evenly spaced from each other.

5. The guidewire handle of claim 3, wherein each aperture of the set of second apertures has a shape that is one of substantially rectangular, square, circular, and triangular.

6. A flushable guidewire assembly comprising:
   a syringe coupled to a guidewire handle;
   the guidewire handle having at least one first hole to allow fluid to flow therethrough; and
   a hub coupled to the guidewire handle a guidewire coupled to the guidewire handle.

7. The flushable guidewire assembly of claim 6, wherein the guidewire handle has a second hole to receive the guidewire.

8. The flushable guidewire assembly of claim 6, wherein the first hole is one of substantially rectangular, square, circular, and triangular.

9. A method comprising:
   coupling a hub to a guidewire handle and to a syringe, the hub and the guidewire handle have at least one aperture to allow fluid to flow therethrough the guidewire handle attached to a guidewire; and
   flushing a fluid through the flushable guidewire assembly.

10. The method of claim 9, wherein the guidewire handle has a set of apertures configured to receive fluid.

11. The method of claim 9, wherein the at least one aperture is one of substantially rectangular, square, circular, and triangular.

* * * * *